US008968324B2

(12) United States Patent
Atkinson et al.

(10) Patent No.: US 8,968,324 B2
(45) Date of Patent: Mar. 3, 2015

(54) ADJUSTABLE JIG AND METHOD FOR TARGETING INTERLOCKING HOLES OF AN INTRAMEDULLARY NAIL

(75) Inventors: Patrick Atkinson, Grand Blanc, MI (US); Adam Nicholas Garlock, Shelby Township, MI (US)

(73) Assignee: Kettering University, Flint, MI (US)

( * ) Notice: Subject to any disclaimer, the term of this patent is extended or adjusted under 35 U.S.C. 154(b) by 678 days.

(21) Appl. No.: 13/282,570

(22) Filed: Oct. 27, 2011

(65) Prior Publication Data

US 2013/0110119 A1     May 2, 2013

(51) Int. Cl.
*A61B 17/90*     (2006.01)
*A61B 17/17*     (2006.01)

(52) U.S. Cl.
CPC .................................. *A61B 17/1725* (2013.01)
USPC ........................... 606/98; 606/104; 408/115 R

(58) Field of Classification Search
CPC .. A61B 17/175; A61B 17/3403; A61B 19/20; A61B 19/201; A61B 19/203; A61B 2017/3405; A61B 2017/3411
USPC ........... 606/62–64, 86 R, 96–98, 102, 104, 1, 606/129, 130; 600/196, 215; 269/47, 48, 269/49, 50, 51, 52; 408/115, 115 R
See application file for complete search history.

(56) References Cited

U.S. PATENT DOCUMENTS 1,476,611 A * 12/1923 Hines ............................... 408/88
2,029,650 A * 2/1936 Betz ............................. 408/115 R
4,541,424 A 9/1985 Grosse et al.
4,667,664 A 5/1987 Taylor et al.
4,865,025 A * 9/1989 Buzzi et al. ..................... 606/96
4,881,535 A 11/1989 Sohngen
4,913,137 A 4/1990 Azer et al.
5,281,224 A 1/1994 Faccioli et al.
5,433,720 A 7/1995 Faccioli et al.
5,620,449 A 4/1997 Faccioli et al.
5,776,179 A 7/1998 Ren et al.
6,494,913 B1 12/2002 Huebner
7,066,943 B2 6/2006 Zirkle et al.
7,214,008 B1 * 5/2007 Dods et al. ................ 408/115 R
7,297,163 B2 11/2007 Huebner
7,338,492 B2 3/2008 Singhatat et al.
2004/0082955 A1 4/2004 Zirkle, Jr.
2004/0215204 A1 10/2004 Davison et al.

(Continued)

FOREIGN PATENT DOCUMENTS

WO         0189395 A2     11/2001
WO    2004069063 A1     8/2004

*Primary Examiner* — Todd Manahan
*Assistant Examiner* — Marcela I Shirsat
(74) *Attorney, Agent, or Firm* — Dickinson Wright, PLLC

(57) ABSTRACT

A targeting jig apparatus for targeting interlocking holes of an intramedullary nail. The targeting jig includes a support-arm extending substantially parallel to the intramedullary nail. A targeting mechanism including a pair of targeting mechanism drill-guide orifices is adjustably disposed on the support arm for aligning the targeting mechanism drill-guide orifice with the interlocking holes of the intramedullary nail. The targeting mechanism includes a saddle having a U-shape including a base and parallel legs that are slidable along the support-arm. A connection mechanism includes a horizontal slot on the support-arm aligned with a vertical slot on the targeting mechanism and a pivot screw extending through the slots for facilitating adjustment of the targeting mechanism relative to the support arm.

18 Claims, 4 Drawing Sheets

(56) References Cited

U.S. PATENT DOCUMENTS

| | | |
|---|---|---|
| 2006/0064106 A1 | 3/2006 | Fernandez |
| 2006/0184173 A1 | 8/2006 | Collazo |
| 2008/0264109 A1 | 10/2008 | Ritchey et al. |
| 2009/0069816 A1 | 3/2009 | Sasing et al. |
| 2009/0306665 A1 | 12/2009 | Lerner et al. |

* cited by examiner

ADJUSTABLE JIG AND METHOD FOR TARGETING INTERLOCKING HOLES OF AN INTRAMEDULLARY NAIL

STATEMENT REGARDING FEDERALLY SPONSORED RESEARCH

This invention was made with Government support under contract numbers W81XWH0720119 and W81XWH1120128 awarded by the Unites States Army Medical Research Acquisition Activity. The Government has certain rights in this invention.

BACKGROUND OF THE INVENTION

1. Field of the Invention

A targeting jig apparatus for targeting interlocking holes of an intramedullary nail.

2. Description of the Prior Art

It is well known in the art to use intramedullary nails to stabilize bone fractures. The intramedullary nail is inserted into the medullary canal of the bone across the fracture site in order to align the bone fragments with one another and prevent the bone fragments from being displaced during healing. The intramedullary nail typically includes interlocking through holes at the distal and proximal ends of the nail that are in alignment with holes drilled into the bone of the patient. Tightening screws are threaded through the holes in the bone of the patient and pass through the interlocking holes to hold the bone fragments in place. A common difficulty in the art relates to locating a bone drill-guide with the interlocking holes in the intramedullary nail, particularly at the end of the nail remote to the incision and after implantation into the bone of the patient.

Adjustable targeting jigs are well known in the art for locating the bone drill-guide with the interlocking holes in the nail prior to implantation of the intramedullary nail, such that after implantation the holes are located. One such adjustable jig is disclosed in U.S. Pat. No. 4,667,664 and includes a support-arm extending along a support-arm axis from a support-arm proximal end to a support-arm distal end and spaced from and substantially parallel to the intramedullary nail. A targeting mechanism is disposed on the support-arm for adjustment of the targeting mechanism relative to the support-arm and defining a targeting mechanism drill-guide orifice for aligning the targeting mechanism drill-guide orifice with one of the interlocking holes of the intramedullary nail.

Known problems with the current art are that the means for adjustment of the targeting jig are generally complicated leading to increased costs and difficulties in use.

SUMMARY OF THE INVENTION

The subject invention provides such a targeting jig apparatus wherein the targeting mechanism includes a saddle having a U-shape including a base and parallel legs slidable along the support-arm and a connection mechanism interconnecting the legs of the saddle and the support-arm for adjusting the targeting mechanism relative to the support-arm for aligning the targeting mechanism drill-guide orifice with one of the interlocking holes of the intramedullary nail.

The subject invention also provides for a method of targeting interlocking holes of an intramedullary nail using a targeting jig apparatus including the step of sliding the targeting mechanism relative to the support-arm parallel to the support-arm axis and along a vertical axis extending perpendicular to the base of the saddle and rotating the targeting mechanism relative to the support-arm about an adjustment axis extending through the legs of the targeting mechanism by the connection mechanism to provide for coarse alignment of one of the drill-guide orifices with one of the interlocking holes of the intramedullary nail.

ADVANTAGES OF THE INVENTION

Thus several advantages of one or more aspects of the invention are that the targeting jig allows for adjustment in three degrees of freedom while being comprised of very few parts leading to an inexpensive, easy to assemble and easy to operate jig that can accommodate a wide range of intramedullary nails.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE ENABLING EMBODIMENTS

Figure 1:
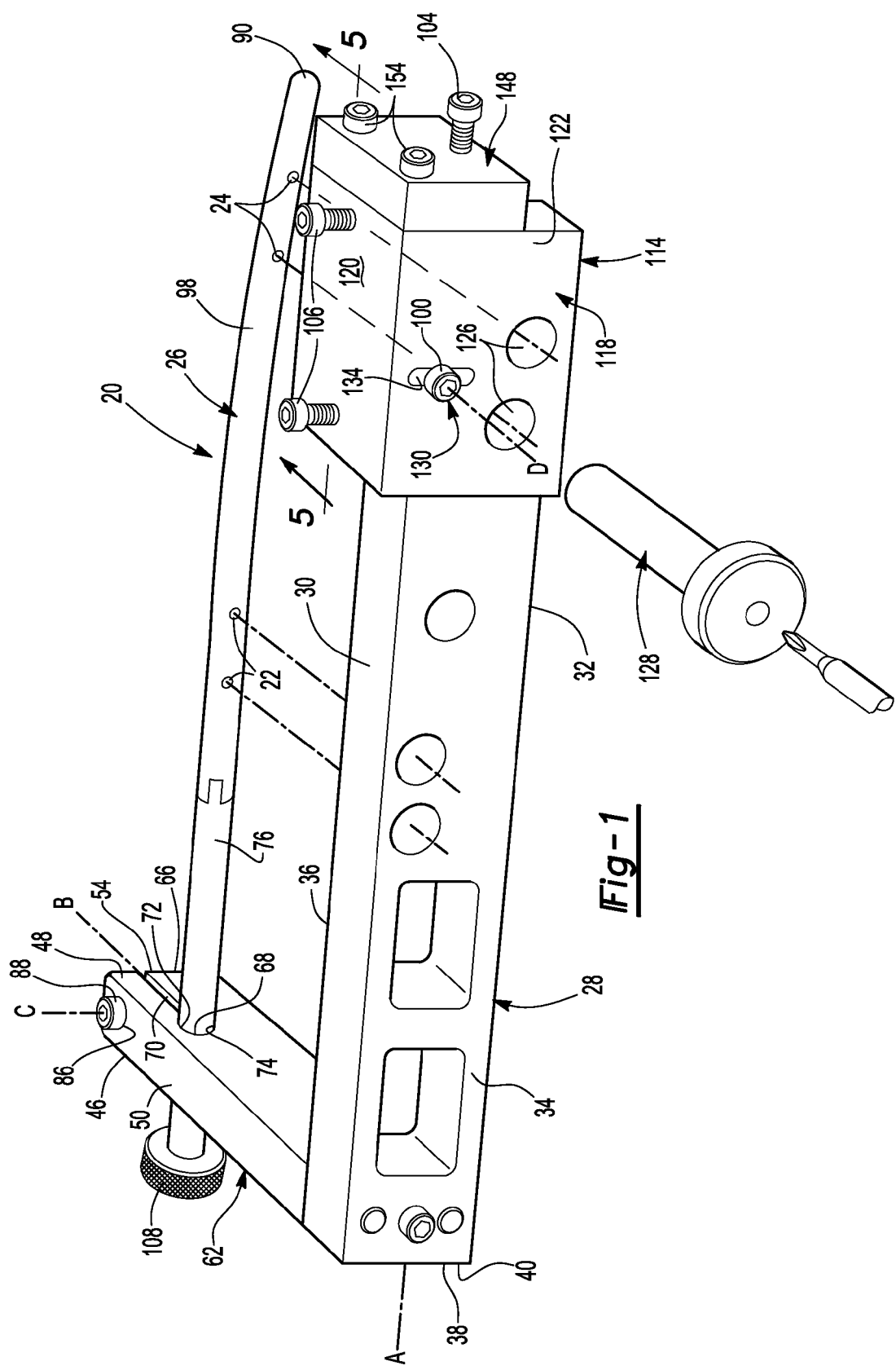
FIG. 1 is a perspective view of the apparatus of the first enabling embodiment.
Figure 2:
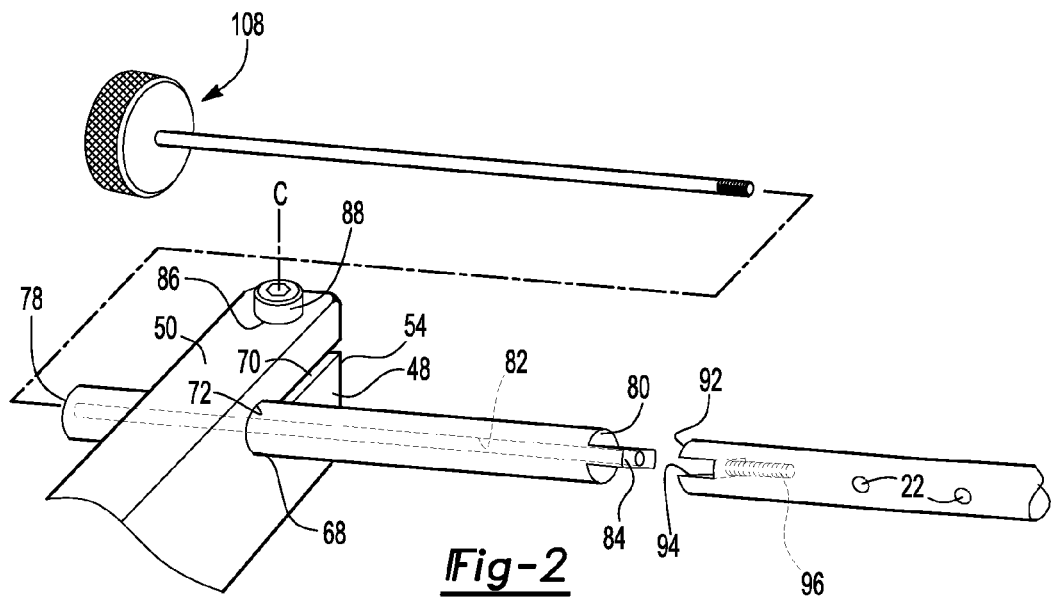
FIG. 2 is a perspective view of the support leg, nail guide, intamedullary nail, and nail-locking rod with the nail-locking rod and intramedullary nail disconnected from the assembly.
Figure 3:
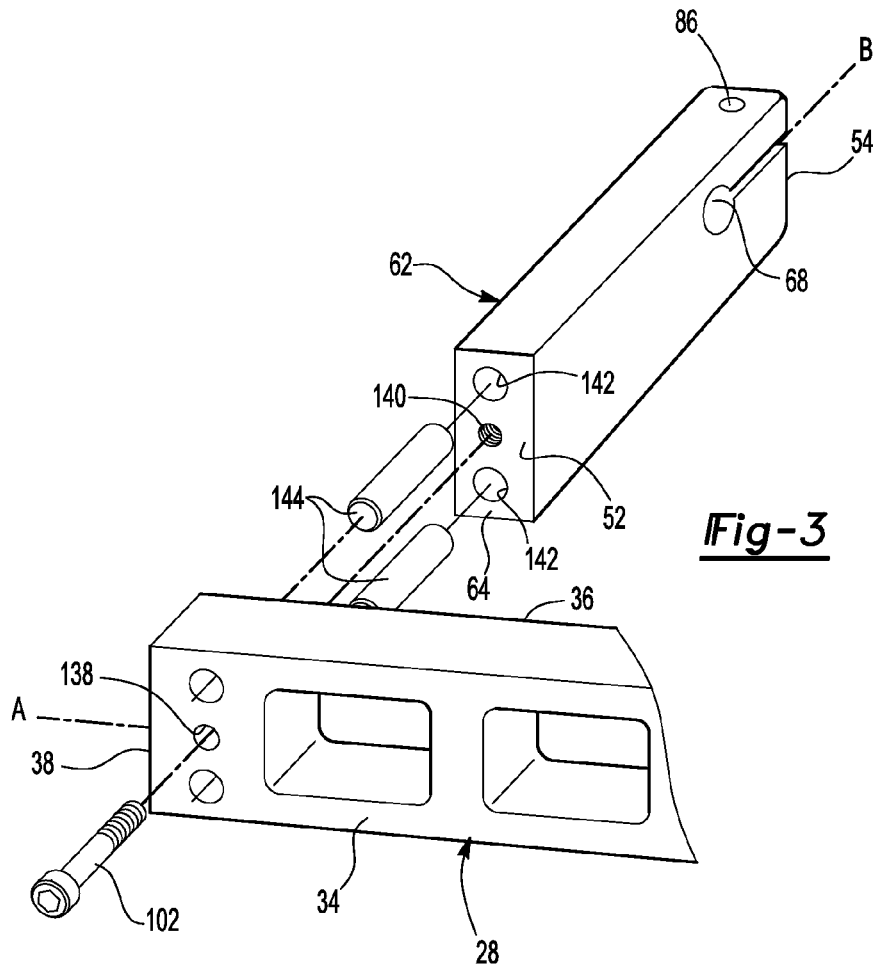
FIG. 3 is a perspective view of the support-arm and support-leg of the first enabling embodiment with the support-arm disconnected from the support-leg.
Figure 4:
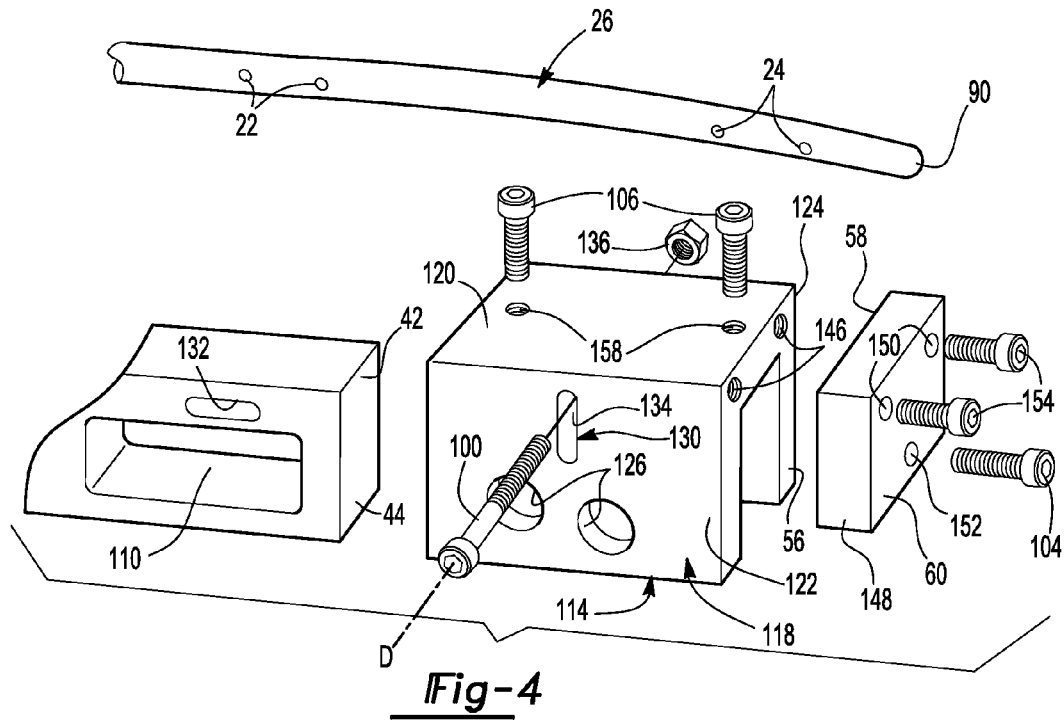
FIG. 4 is an exploded view of the intramedullary nail, support arm and targeting mechanism of the first enabling embodiment.
Figure 5:
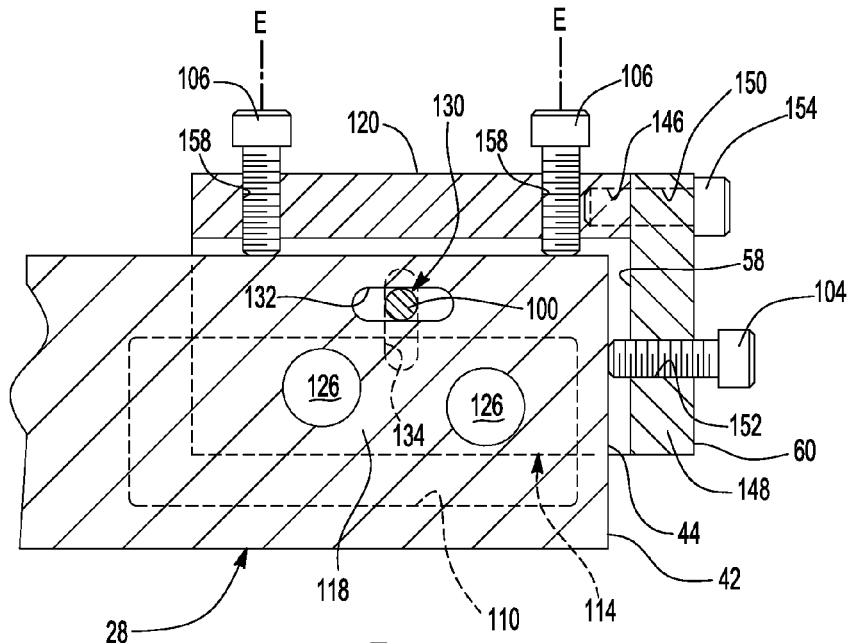
FIG. 5 is a cross-sectional view of the support arm and targeting mechanism taken along 5-5 of FIG. 1.

Referring to the Figures, wherein like numerals indicate corresponding parts throughout the several views, a targeting jig apparatus 20 for targeting interlocking holes 22, 24 of an intramedullary nail 26 is generally shown.

The targeting jig apparatus 20 includes a support-arm 28 that has a rectangular cross-section and defines a support-arm upper face 30, a support-arm lower face 32, a support-arm front face 34 and a support-arm rear face 36. The support-arm 28 extends along a support-arm axis A from a support-arm proximal end 38 that defines a support-arm proximal face 40 to a support-arm distal end 42 that defines a support-arm distal face 44. It should be appreciated that the support-arm 28 could have other cross sections with corresponding alternate faces.

A support-leg 62 that has a rectangular cross section engages the support-arm 28 adjacent the support-arm proximal end 38 and includes a support-leg proximal face 46, a support-leg distal face 48, and a support-leg upper face 50. The support-leg 62 extends perpendicularly from the support-arm axis A along a support-leg axis B from a support-leg front end 64 that defines a support-leg front face 52 to a support-leg rear end 66 that defines a support-leg rear face 54. It should be appreciated that the support-leg 62 could also have other cross sections with corresponding alternate faces.

The support-leg 62 further defines a support-leg bore 68 extending parallel to the support-arm axis A from the support-leg proximal face 46 to the support-leg distal face 48 adjacent the support-leg rear end 66. A support-leg slot 70 extends through the support-leg bore 68 parallel to the support-leg upper face 50 and divides the support-leg bore 68 to present a first semi-cylindrical surface 72 and a second semi-cylindrical surface 74. A nail-guide 76 is partially disposed in the support-leg bore 68. The nail-guide 76 has a cylindrical shape and extends parallel to the support-arm axis A from a nail-guide proximal end 78 to a nail-guide distal end 80, and the nail-guide 76 defines a nail-guide bore 82 extending from the nail-guide proximal end 78 to the nail-guide distal end 80. Further, a locking tab 84 extend from the nail-guide distal end 80.

The support-leg 62 further defines a threaded nail-guide tightening screw bore 86 that extends along a tightening screw bore axis C from the support-leg upper face 50 and through the support-leg slot 70 adjacent the support-leg rear face 54. A nail-guide tightening screw 88 threadedly engages the nail-guide tightening screw bore 86 for drawing the semi-cylindrical surfaces 72, 74 towards each other to clamp the nail-guide 76 to the support-leg 62. It should be appreciated that the support leg bore 62 can receive nail-guides 76 of various sizes to provide for the use of various sized and shaped intramedullary nails 26.

The intramedullary nail 26 extends from a nail distal end 90 to a nail proximal end 92, wherein the nail proximal end 92 defines a locking slot 94 for receiving the locking tab 84 of the nail-guide 76 to couple the intramedullary nail 26 and the nail-guide 76 at a predetermined orientation corresponding to the position of the locking tab 84 and locking slot 94. It should be appreciated that more or fewer locking slots 94 and tabs 84 with various shapes could be used. The intramedullary nail 26 further defines a threaded nail bore 96 extending into the intramedullary nail 26 from the nail proximal end 92. Additionally, the intramedullary nail 26 defines a nail outer surface 98 that defines a pair of threaded proximal end interlocking holes 22 adjacent the nail proximal end 92 and a pair of threaded distal end interlocking holes 24 adjacent the nail distal end 90 for receiving a tightening screw. It should be appreciated that more or fewer interlocking holes 22, 24 could be on the nail at various locations of the intramedullary nail 26. Two skeletal fixation systems including improvements related to the interlocking holes and tightening screws are disclosed in Ser. Nos. 12/90172 and 12/818395. It should be appreciated that the subject invention can be used in conjunction with or without the systems disclosed in the aforementioned U.S. patent applications. A threaded nail-locking rod 108 extends through the nail-guide bore 82 and threadedly engages the nail bore 96 for securing the nail-guide 76 to the intramedullary nail 26. It should be appreciated that intramedullary nails 26 of various sizes and shapes could be used with the targeting jig apparatus 20.

The support-arm 28 further defines at least one support-arm drill-guide passage 110 having a rectangular shape that extends from the support-arm front face 34 to the support-arm rear face 36 at a location adjacent the support-arm lower face 32. It should be appreciated that any quantity of drill-guide passages 110 with various shapes and sizes could be defined at different locations of the support-arm 28. However, the support-arm drill-guide passages 110 should be aligned with the interlocking holes 22, 24 of the intramedullary nail 26.

At least one targeting mechanism 114, 116 is adjustably disposed on the support-arm 28. The targeting mechanism 114, 116 includes a saddle 118 that has a U-shape defining a base 120 that is movably spaced from the support-arm upper face 30, a front leg 122 that is slidable along the support-arm front face 34 and a rear leg 124 that is slidable along the support-arm rear face 36. The front and rear legs 122, 124 of the targeting mechanism 114, 116 each define a pair of the targeting mechanism drill-guide orifices 126. The targeting mechanism drill-guide orifices 126 are each smaller than the arm drill-guide passage 110 such that the targeting mechanism drill-guide orifices 126 can be aligned with the interlocking holes 22, 24 of the intramedullary nail 26 without being blocked by the support-arm 28 after adjustment of the targeting mechanism 114, 116 relative to the support-arm 28. A drill-guide cylinder 128 is for slidably extending through one of the targeting mechanism drill-guide orifices 126 and one of the drill-guide orifices for alignment with one of the interlocking holes 22, 24 of the intramedullary nail 26 for tightening fixing screws into the holes 22, 24 of the intramedullary nail 26. The base 120 of the saddle 118 defines a pair of threaded vertical-adjustment screw bores 158 extending parallel to the tightening screw bore axis C through the body 120 of the saddle 118 along a vertical axis E and a pair of vertical-adjustment screws 106 threadedly extend through the vertical-adjustment screw bores 158 and engage the support-arm 28 for fine adjustment of the distal end targeting mechanism 114 relative to the support-arm 28 parallel to the vertical axis E.

A connection mechanism 130 for connecting the targeting mechanism 114, 116 and the support-arm 28 and for adjusting the targeting mechanism 114, 116 relative to the support-arm 28 defines a horizontal-adjustment slot 132 that extends from the support-arm front face 34 to the support-arm rear face 36 adjacent the support-arm upper face 30. The connection mechanism 130 further defines a vertical-adjustment slot 134 defined by the front leg 122 and the rear leg 124 of the at least one targeting mechanism 114, 116 for alignment with the horizontal-adjustment slot 132 of the support-arm 28 on an adjustment axis D. The connection mechanism 130 also includes a pivot screw 100 that extends along the adjustment axis D through the vertical-adjustment slots 134 of the targeting mechanism 114, 116 and the horizontal-adjustment slot 132 of the support-arm 28 for facilitating adjustment of the targeting mechanism 114, 116 relative to the support-arm 28 in directions parallel to the support-arm axis A and parallel to the tightening screw bore axis C and for rotational about the adjustment axis D. The connection mechanism 130 further including a nut 136 threadedly engaging the pivot screws 100 for fastening the targeting mechanism 114, 116 to the support-arm 28 at a desired position.

In a first enabling embodiment as best shown in FIGS. 1-5, the support-arm drill-guide passage 110 is defined at a location adjacent the support-arm distal end 42. The support-arm 28 further defines a support-arm proximal bore 138 that extends parallel to the support-leg axis B from the support-arm front face 34 to the support-arm rear face 36 at a location adjacent the support-arm proximal end 38. The support-leg 62 further defines a threaded support-leg front face bore 140 and a pair of support-leg dowel bores 142 extending parallel to the support-leg axis B into the support-leg 62 from the support-leg front face 52. A pair of support-arm dowels 144 extend parallel to the support-leg axis B from the support-arm rear face 36 adjacent the support-arm proximal end 38 for fitting into the support-leg dowel bores 142 for aligning the support-arm 28 and support-leg 62 at a fixed orientation. Further, a support-leg engagement screw 102 extends through the support-arm proximal bore 138 and threadedly engages the support-leg front face bore 140 of the support-leg 62 for securing the support-leg front face 52 to the support-arm rear face 36.

Additionally, in the first enabling embodiment, the targeting mechanism 114, 116 is a distal end targeting mechanism 114 disposed on the support-arm 28 adjacent the support-arm distal face 44. The base 120 and legs 122, 124 of the distal end targeting mechanism 114 define a targeting mechanism distal face 56. The targeting mechanism distal face 56 defines a pair of threaded targeting mechanism bores 146 each extending parallel to the support-arm axis A through the distal end targeting mechanism 114 from the targeting mechanism distal face 56. An axial-adjustment support 148 having a rectangular cross section extends from an axial-adjustment support proximal face 58 that engages the targeting mechanism distal face 56 to an axial-adjustment support distal face 60. The axial-adjustment support 148 defines a pair of support-screw bores 150 and a threaded axial-adjustment screw bore 152, each extending through the axial-adjustment support 148 from the axial-adjustment support proximal face 58 to the axial-adjustment support distal face 60. A pair of support-screws 154 each extend through one of the support-screw bores 150 and threadedly engage one of the targeting mechanism bores 146 for securing the axial-adjustment support 148 to the targeting mechanism 114. Further, an axial-adjustment screw 104 threadedly extends through the axial-adjustment screw bore 152 and abuts the support-arm distal face 44 for fine adjustment parallel to the support-arm axis A of the distal end targeting mechanism 114 relative to the support-arm 28.

Figure 6:
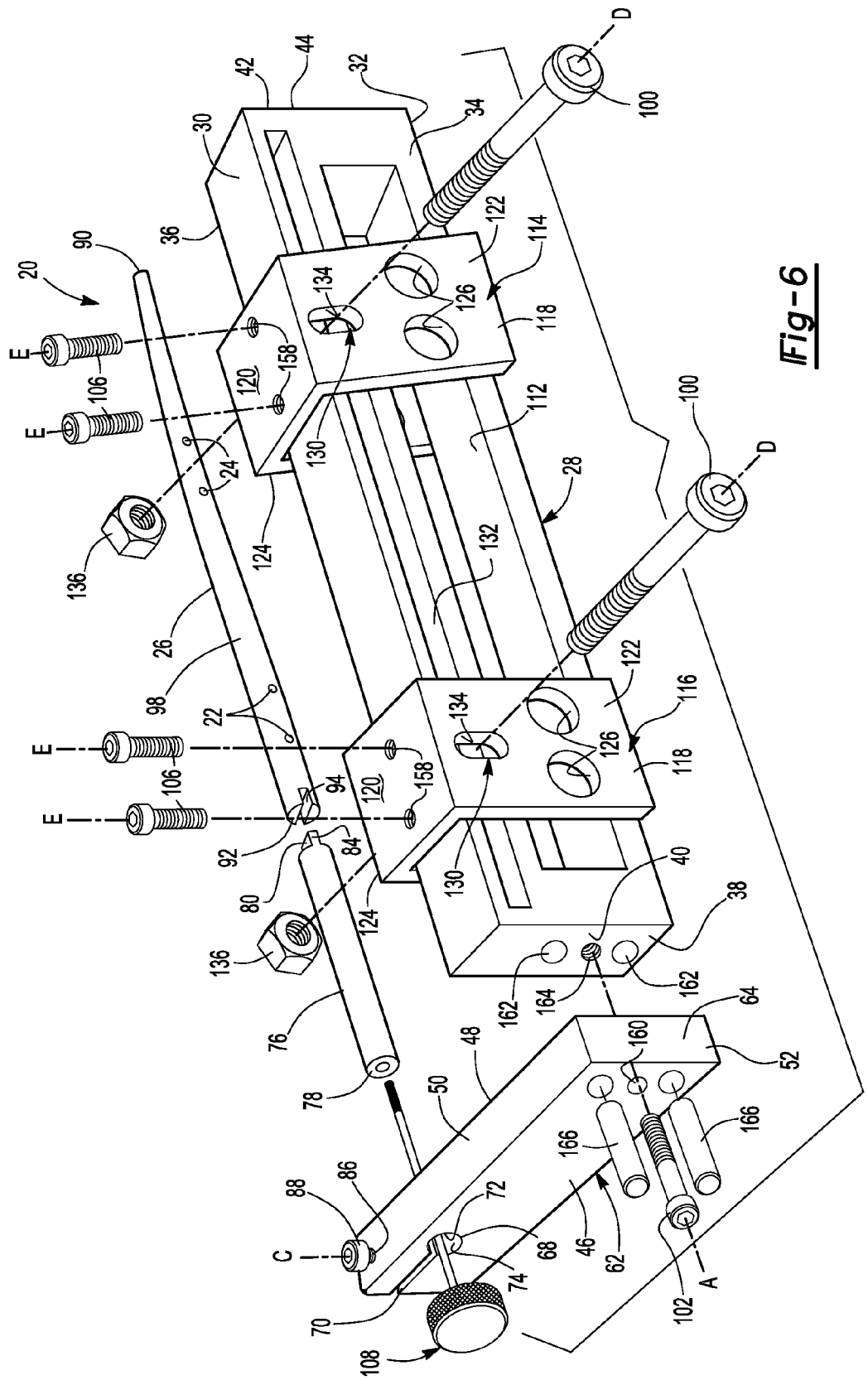
FIG. 6 is a partially exploded perspective view of the second enabling embodiment.

In a second enabling embodiment as best shown in FIG. 6, the support-arm drill-guide passage 110 extends from a location adjacent the support-arm distal end 42 to a location adjacent the support-arm proximal end 38. Further, the support-leg 62 defines a support-leg front end bore 160 extending parallel to the support-arm axis A from the support-leg proximal face 46 to the support-leg distal face 48 adjacent the support-arm front end 64. The support-arm 28 defines a pair of support-arm dowel bores 162 and a threaded support-arm proximal end bore 164, each extending parallel to the support-arm axis A into the support-arm 28 from the support-arm proximal face 40. A pair of support-leg dowels 166 extend parallel to the support-arm axis A from the support-leg distal face 48 adjacent the support-leg front end 64 for fitting into the support-arm dowel bores 162. A support-leg engagement screw 102 extends through the support-leg front end bore 160 and threadedly engages the support-arm proximal end bore 164 for securing the support-leg distal face 48 to the support-arm proximal face 40. It should be appreciated that other means for attaching the support-arm 28 and support-leg 62 could be used.

Additionally, in the second enabling embodiment, a proximal end targeting mechanism 116 is disposed on the support-arm 28 adjacent the support-arm proximal end 38 and a distal end targeting mechanism 114 is disposed on the support-arm 28 adjacent the support-arm distal end 42. It should be appreciated that any number of targeting mechanisms 114, 116 could be used on the jig.

A method for targeting interlocking holes 22, 24 of an intramedullary nail 26 using a targeting jig apparatus 20 is also included. The method begins with the step of inserting the pivot screw 100 through the vertical-adjustment slots 134 of the targeting mechanism 114, 116 and the horizontal-adjustment slot 132 of the support-arm 28.

The method proceeds with a coarse alignment step for coarse alignment of at least one of the drill guide passages 110, 112 and drill-guide cylinder 128 with one of the interlocking holes 22, 24 of the intramedullary nail 26. The coarse alignment step includes sliding the targeting mechanism 114, 116 relative to the support-arm 28 in directions parallel to the support-arm axis A and parallel to the vertical axis E and rotating the targeting mechanism 114, 116 relative to the support-arm 28 about the adjustment axis D by the pivot screw 100 such that the drill-guide cylinder 128 is substantially aligned with one of the interlocking holes 22, 24 of the intramedullary nail 26.

The method proceeds with a fine alignment step for fine alignment of at least one of the drill guide passages 110, 112 and drill-guide cylinder 128 with one of the interlocking holes 22, 24 of the intramedullary nail 26. The step includes adjusting the axial-adjustment screw 104 for moving the targeting mechanism 114 relative to the support-arm 28 in a direction parallel to the support-arm axis A. The step proceeds with adjusting the vertical-adjustment screw 106 for moving the targeting mechanism 114, 116 relative to the support-arm 28 in a direction parallel to the vertical axis E, The method proceeds with threadedly securing the nut 136 to the pivot screw 100 for fastening the targeting mechanism 114, 116 to the support-arm 28.

Obviously, many modifications and variations of the present invention are possible in light of the above teachings and may be practiced otherwise than as specifically described while within the scope of the appended claims. The use of the word "said" in the apparatus claims refers to an antecedent that is a positive recitation meant to be included in the coverage of the claims whereas the word "the" precedes a word not meant to be included in the coverage of the claims.

What is claimed is:

1. A targeting jig apparatus for targeting interlocking holes of an intramedullary nail comprising;
   a support-arm extending along a support-arm axis from a support-arm proximal end to a support-arm distal end for being spaced from and substantially parallel to the intramedullary nail,
   said support-arm defining a first adjustment slot,
   at least one targeting mechanism disposed on said support-arm and defining at least one targeting mechanism drill-guide orifice for being aligned with one of the interlocking holes of the intramedullary nail,
   said at least one targeting mechanism including a saddle having a U-shape including a base and parallel legs slidable along said support-arm,
   each of said legs of said saddle defining a second adjustment slot for alignment with said first adjustment slot of said support arm along an adjustment axis, and
   a connection mechanism interconnecting said legs of said saddle and said support-arm for said adjustment of said targeting mechanism relative to said support-arm and for aligning of said at least one targeting mechanism drill-guide orifice with one of the interlocking holes of the intramedullary nail.

2. The apparatus as set forth in claim 1 wherein said first adjustment slot in said support-arm is a horizontal adjustment slot and said second adjustment slot in each of said legs of said saddle is a vertical adjustment slot.

3. The apparatus as set forth in claim 2 wherein said connection mechanism further includes a pivot screw extending along said adjustment axis through said vertical-adjustment slots and said horizontal-adjustment slot for facilitating said adjustment of said targeting mechanism relative to said support-arm and said adjustment of said targeting mechanism being perpendicular to said base of said saddle along a vertical axis and parallel to said support-arm axis and for rotation about said adjustment axis.

4. The apparatus as set forth in claim 3 wherein said connection mechanism further includes a nut threadedly engaging said pivot screw for fastening said targeting mechanism to said support-arm.

5. The apparatus as set forth in claim 3 wherein said body of said saddle defines a pair of vertical-adjustment screw bores having threads and extending through said body of said saddle to define said vertical axis.

6. The apparatus as set forth in claim 5 wherein a pair of vertical-adjustment screws threadedly extend through said vertical-adjustment screw bores and engage said support-arm for fine adjustment of said distal end targeting mechanism relative to said support-arm parallel to said vertical axis.

7. The apparatus as set forth in claim 1 wherein said support-arm defines a support-arm upper face and a support-arm front face and a support-arm rear face and said base of said saddle is movably spaced from said support-arm upper face and said parallel legs of said targeting mechanism include a front leg slidable along said support-arm front face and a rear leg slidable along said support-arm rear face.

8. The apparatus as set forth in claim 1 wherein said front leg and said rear leg of said targeting mechanism each define a pair of said targeting mechanism drill-guide orifices.

9. The apparatus as set forth in Claim 1 wherein said at least one targeting mechanism is a distal end targeting mechanism disposed on said support-arm adjacent said support-arm distal end.

10. The apparatus as set forth in claim 1 wherein said at least one targeting mechanism is a proximal end targeting mechanism disposed on said support-arm adjacent said support-arm proximal end.

11. The apparatus as set forth in claim 1 wherein said support-arm defines at least one arm drill-guide passage extending from said support-arm front face to said support-arm rear face.

12. The apparatus as set forth in claim 11 wherein said arm drill guide passage has a rectangular shape.

13. The apparatus as set forth in claim 12 wherein said at least one arm drill-guide passage extends from a location adjacent said support-arm distal end to a location adjacent said support-arm proximal end.

14. A targeting jig apparatus for targeting interlocking holes of an intramedullary nail comprising;
   a support-arm extending along a support-arm axis from a support-arm proximal end to a support-arm distal end for being spaced from and substantially parallel to the intramedullary nail,
   at least one targeting mechanism disposed on said support-arm and defining at least one targeting mechanism drill-guide orifice for being aligned with one of the interlocking holes of the intramedullary nail,
   said at least one targeting mechanism including a saddle having a U-shape including a base and parallel legs slidable along said support-arm,
   said at least one targeting mechanism being a distal end targeting mechanism disposed on said support-arm adjacent said support-arm distal end,
   said base and legs of said distal end targeting mechanism defining a targeting mechanism distal face defining a pair of targeting mechanism bores having threads each extending parallel to said support-arm axis through said distal targeting mechanism from said targeting mechanism distal face, and
   a connection mechanism interconnecting said legs of said saddle and said support-arm for said adjustment of said targeting mechanism relative to said support-arm and for aligning of said at least one targeting mechanism drill-guide orifice with one of the interlocking holes of the intramedullary nail.

15. The apparatus as set forth in claim 14 wherein said distal end targeting mechanism further includes an axial-adjustment support having a rectangular cross section and extending from an axial-adjustment support proximal face engaging said targeting mechanism distal face to an axial-adjustment support distal face.

16. The apparatus as set forth in claim 15 wherein said axial-adjustment support defines a pair of support-screw bores and an axial-adjustment screw bore having threads each extending through said axial-adjustment support from said axial-adjustment support proximal face to said axial-adjustment support distal face.

17. The apparatus as set forth in claim 16 wherein a pair of support-screws each extend through one of said support-screw bores and threadedly engage one of said targeting mechanism bores for securing said axial-adjustment support to said targeting mechanism.

18. The apparatus as set forth in claim 17 wherein an axial-adjustment screw threadedly extends through said axial-adjustment screw bore and abuts said support-arm distal face for fine adjustment parallel to said support-arm axis of said distal portion targeting mechanism relative to said support-arm.

* * * * *